United States Patent
Decoster et al.

(10) Patent No.: US 7,740,873 B2
(45) Date of Patent: *Jun. 22, 2010

(54) COMPOSITION COMPRISING A QUATERNARY SILICONE AND A LIQUID FATTY ALCOHOL AND METHOD OF TREATMENT

(75) Inventors: Sandrine Decoster, Saint Gratien (FR); Benedicte Cazin, Clichy (FR)

(73) Assignee: L'Oreal, Paris (FR)

( * ) Notice: Subject to any disclaimer, the term of this patent is extended or adjusted under 35 U.S.C. 154(b) by 883 days.

This patent is subject to a terminal disclaimer.

(21) Appl. No.: 10/606,786

(22) Filed: Jun. 27, 2003

(65) Prior Publication Data

US 2004/0131576 A1 Jul. 8, 2004

Related U.S. Application Data

(60) Provisional application No. 60/393,831, filed on Jul. 8, 2002.

(30) Foreign Application Priority Data

Jun. 28, 2002 (FR) .................................. 02 08143

(51) Int. Cl.
*A61K 8/02* (2006.01)
*A61K 8/73* (2006.01)
*A61K 8/81* (2006.01)
*A61K 31/695* (2006.01)
*C11D 1/62* (2006.01)
*A01N 55/00* (2006.01)
*A61Q 5/06* (2006.01)
*A61Q 5/00* (2006.01)
*A61Q 9/00* (2006.01)

(52) U.S. Cl. ................. 424/401; 424/70.13; 424/70.15; 424/70.17; 424/70.19; 424/70.21; 424/70.22; 424/70.28; 424/70.31; 514/63; 514/881; 514/941

(58) Field of Classification Search ............. 424/70.12, 424/70.13, 70.15, 70.17, 70.19, 70.21, 70.22, 424/70.28, 70.31, 401; 514/63, 881, 941
See application file for complete search history.

(56) References Cited

U.S. PATENT DOCUMENTS

| | | | | |
|---|---|---|---|---|
| 4,390,522 | A | * | 6/1983 | Jacquet et al. ................. 424/45 |
| 5,180,584 | A | * | 1/1993 | Sebag et al. ................. 510/122 |
| 5,556,615 | A | * | 9/1996 | Janchitraponvej et al. ........................ 424/70.11 |
| 5,876,705 | A | * | 3/1999 | Uchiyama et al. ......... 424/70.12 |
| 5,989,533 | A | | 11/1999 | Deegan et al. |
| 6,214,326 | B1 | * | 4/2001 | Dupuis ........................ 424/70.1 |
| 6,224,888 | B1 | * | 5/2001 | Vatter et al. ................. 424/401 |
| 6,231,877 | B1 | * | 5/2001 | Vacher et al. ............... 424/401 |

FOREIGN PATENT DOCUMENTS

| | | |
|---|---|---|
| EP | 0 968 709 | 1/2000 |
| GB | 2173515 | 10/1986 |
| WO | WO 01/82879 | 11/2001 |

OTHER PUBLICATIONS

Monick (J. Am. Oil Chemists Soc 1979, 56, 853A-860A).*

* cited by examiner

*Primary Examiner*—Ernst V Arnold
(74) *Attorney, Agent, or Firm*—Oblon, Spivak, McClelland, Maier & Neustadt, L.L.P.

(57) ABSTRACT

Composition containing at least one silicone with quaternary ammonium groups and at least one liquid fatty alcohol. Method for the cosmetic treatment of keratinous materials, in particular hair. The compositions preferably are transparent and have a melting texture. Hair treated with these compositions is shiny, feels soft and is free of residues.

43 Claims, No Drawings

COMPOSITION COMPRISING A QUATERNARY SILICONE AND A LIQUID FATTY ALCOHOL AND METHOD OF TREATMENT

REFERENCE TO PRIOR APPLICATIONS

This application claims priority to U.S. provisional application 60/393,831 filed Jul. 8, 2002, and to French patent application 0208143 filed Jun. 28, 2002, both of which are incorporated herein by reference.

SUMMARY OF THE INVENTION

The present invention relates to a composition, preferably a cosmetic composition, in particular for conditioning hair, comprising a quaternary silicone and at least one liquid fatty alcohol, and to a method for the cosmetic treatment of keratinous materials, in particular hair.

BACKGROUND AND GENERAL DESCRIPTION OF THE INVENTION

It is well known that hair which has been sensitized (i.e. damaged and/or embrittled) to various degrees under the action of atmospheric agents or under the action of mechanical or chemical treatments, such as dyeing, bleaching and/or permanent waving, is often difficult to disentangle and to style, and lacks softness.

The use of cationic polymers, cationic silicones or cationic surfactants to the disentanglement of the hair and to impart softness and suppleness to it has already been recommended in compositions for the washing or care of keratinous materials such as hair. The use of cationic polymers or of cations for this purpose exhibits various disadvantages. Because of their high affinity for the hair, some of these polymers become substantially deposited during repeated use, and lead to undesirable effects such as a lank, unpleasant feel, a stiffening of the hair, and an interfiber adhesion affecting hair styling.

In summary, it is found that current conditioning cosmetic compositions are not completely satisfactory.

Moreover, it is sometimes sought to obtain transparent cosmetic compositions which are particularly appreciated by consumers. Conventional conditioning compositions based on fatty alcohols of the prior art are not transparent.

The inventors have now discovered that the combination of a quaternary silicone and at least one liquid fatty alcohol makes it possible to overcome these disadvantages.

Hair treated with this composition is smooth, is easy to disentangle, is shiny, supple, individualized and has a soft feel and with no residue. The hair has a natural and nonlank look.

In addition, these compositions can be transparent and have a melting texture, that is to say which disappears rapidly into the hair.

Moreover, the compositions of the invention, when applied to the skin, in particular in the form of a foam bath or a shower gel, provide an improvement in the softness of the skin and are easy to rinse off with no unpleasant feel.

DETAILED DESCRIPTION OF THE PREFERRED EMBODIMENTS

Thus, according to the present invention, there are now provided novel compositions comprising, for example in a medium that preferably is a cosmetically acceptable medium, at least one silicone with quaternary ammonium groups and at least one liquid fatty alcohol.

Another subject of the invention is a method for the cosmetic treatment of keratinous materials, in particular hair, using the abovementioned composition.

The subject of the invention is also the use of said composition as an after-shampoo.

The subject of the invention is also the use of said composition for making the hair shiny.

The subject of the invention is also the use of said composition for making the hair supple.

Other subjects, characteristics, aspects and advantages of the invention will appear even more clearly on reading the description and the various examples which follow.

In accordance with the invention, the modifiers "cosmetic" and "cosmetically acceptable" refer to compositions, media, methods, etc., compatible with human keratin, and which can be applied to, e.g., the skin and hair. The cosmetic compositions and methods of the invention are preferred embodiments thereof. These terms sometimes appear within parentheses herein to denote their preferred, but not required, presence.

Silicone with Quaternary Ammonium Groups:

The term "silicone with quaternary ammonium groups" is understood to mean any silicone containing one or more quaternary ammonium groups. These quaternary ammonium groups may be attached in the alpha or omega position or in the form of side groups. They may be attached directly to the polysiloxane backbone or they may be carried by hydrocarbon chains.

According to the invention, silicone is understood to mean, in accordance with what is generally accepted, any polymer having a structure based on the alternation of silicon and oxygen atoms, linked to each other by bonds called siloxane bonds (—Si—O—Si—), and additionally characterized by the existence of silicon-carbon bonds. These silicones, or polysiloxanes, are generally obtained by polycondensation of suitably functionalized silanes. The hydrocarbon radicals most commonly carried by the silicon atoms are lower alkyl, in particular methyl, radicals, fluoroalkyl radicals, aryl, and in particular phenyl, radicals.

The silicones with quaternary ammonium groups of the present invention include compounds corresponding to the following general formulae:

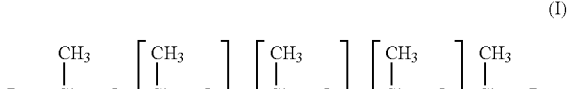

(I)

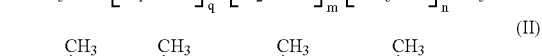

(II)

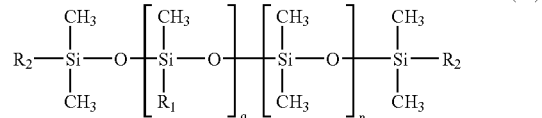

(III)

(IV)

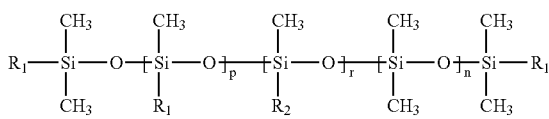

in which formulae:
R₁, which is identical or different, represents a linear or branched $C_1$-$C_{30}$ alkyl group or phenyl group;
R₂, which is identical or different, represents —$C_cH_{2c}$—O—$(C_2H_4O)_a$—$(C_3H_6O)_b$—R₅ or —$C_cH_{2c}$—O—$(C_4H_8O)_a$—R₅;
R₅, which is identical or different, is selected from the group consisting of the groups of the following formula:

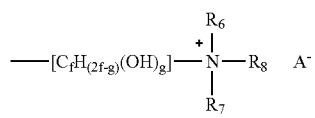

the radicals R₈ independently represent a linear or branched $C_{1-22}$ alkyl or $C_{2-22}$ alkenyl radical, and optionally carrying one or more OH groups, or represent a group $C_hH_{2h}ZCOR_9$;
R₆, R₇ and R₉, which are identical or different, represent linear or branched $C_{1-22}$ alkyl or $C_{2-22}$ alkenyl radicals optionally carrying one or more OH groups, or R₇ may form with part of R₈ a heterocycle (ring with at least one heteroatom such as for example N, O, P), the heterocycle is in particular an imidazoline. Preferably, R₆ and R₇ denote a $C_1$-$C_6$ alkyl radical and more particularly a methyl radical, R₉ preferably denotes a radical selected from the group consisting of $C_8$-$C_{18}$ alkyls and $C_8$-$C_{18}$ alkenyls and in particular a cocoyl radical.
m varies from 0 to 20;
n varies from 0 to 500;
p varies from 1 to 50;
q varies from 0 to 20;
r varies from 1 to 20;
a varies from 0 to 50;
b varies from 0 to 50;
c varies from 0 to 4;
f varies from 0 to 4,
g varies from 0 to 2, preferably is equal to 1
h varies from 1 to 4, preferably is equal to 3
Z represents an oxygen atom or NH,
A⁻ represents a monovalent inorganic or organic anion such as a halide (e.g. chloride, bromide), a sulfate, or a carboxylate (e.g. acetate, lactate, citrate).
Preferably, use is made of the quaternary ammonium containing silicones corresponding to the general formula (III) as defined above, and more particularly those corresponding to general formula (III) in which at least one, preferably all, of the following conditions are satisfied:
c is equal to 2 or 3;
R₁ denotes the methyl group;
a and b are equal to zero;
n varies from 0 to 100;
q is equal to 0;
f=3;
g=1;
R₆ and R₇ denote the methyl group;
R₈ denotes the radical —(CH₂)—NHCOR₉.

Such silicones are marketed for example by the company GOLDSCHMIDT under the names ABIL QUAT 3272, ABIL B 9905, ABIL QUAT 3474 and ABIL K 3270, by the company LIPO FRANCE under the names SILQUAT Q-100, SILQUAT Q-200 WS, SILQUAT AX, SILQUAT AC, SILQUAT AD and SILQUAT AM all manufactured by the company SILTECH, by the company OSI under the name MAGNASOFT EXHAUST and SILSOFT C-880 and by the company UCIB under the names PECOSIL 14-PQ and PECOSIL 36-PQ (manufacturer PHOENIX CHEMICAL).

These silicones are in particular described in Patents EP 530 974, DE 3 719 086, DE 3 705 121, EP 617 607 and EP 714 654.

The silicones with quaternary ammonium groups which are used in accordance with the invention may be provided in the form of aqueous solutions, in the form of dispersions or emulsions in water, etc.

In the compositions of the present invention, the silicone(s) with quaternary ammonium groups are preferably present in an amount of 0.01 to 10% by weight, more preferably in an amount of 0.1 to 5% by weight relative to the total weight of the composition.

Liquid Fatty Alcohol:

The compositions according to the invention additionally comprise at least one liquid fatty alcohol. According to the invention, the fatty alcohol is liquid at room temperature (about 25° C.) and at atmospheric pressure (1 atm).

The liquid fatty alcohols are for example selected from the group consisting of saturated or unsaturated, linear or branched $C_8$-$C_{30}$, preferably C12-C20, fatty alcohols; they are optionally oxyalkylenated with 1 to 15 mol of C2-C4 alkylene oxide, preferably 1 to 5 and more particularly 2 to 4 mol of alkylene oxide or polyglycerolated with 1 to 6 mol of glycerol. The alkylene oxide is preferably ethylene oxide.

The liquid fatty alcohols are preferably selected from the group consisting of linear and saturated $C_8$-$C_{14}$ fatty alcohols, saturated or unsaturated, branched, preferably C12-C30, fatty alcohols; linear and unsaturated C14-C30 fatty alcohols; they are optionally oxyalkylenated with 1 to 15 mol of C2-C4 alkylene oxide, preferably 1 to 5 and more particularly 2 to 4 mol of alkylene oxide.

The oxyalkylenated fatty alcohols are preferably selected from the group consisting of C8-C30 fatty alcohols oxyethylenated with 2 to 6 mol (preferably 2 to 4 mol) of ethylene oxide and in particular C8-C20 linear alcohols oxyethylenated with 2 to 6 mol (preferably 2 to 4 mol) of ethylene oxide.

More particularly, the liquid fatty alcohols are selected from the group consisting of lauryl alcohol (1-dodecanol), myristyl alcohol (1-tetradodecanol), isostearyl alcohol, isocetyl alcohol and oleyl alcohol, lauryl alcohols oxyethylenated with 2 to 6 mol (preferably 2 to 4 mol) of ethylene oxide, in particular linear lauryl alcohols oxyethylenated with 2 to 6 mol (preferably 2 to 4 mol) of ethylene oxide, and mixtures thereof.

The liquid fatty alcohol is preferably present in the compositions of the invention in quantities ranging from 0.01% to 15% by weight relative to the total weight of the composition, and more preferably from 0.1 to 5% by weight and still more particularly from 0.15 to 3% by weight, and still even more particularly from 0.25 to 2% by weight relative to the total weight of the composition.

Other Ingredients:

According to a preferred embodiment of the invention, the compositions may be substantially free of solid fatty alcohols, that is to say that they comprise less than 0.5% by weight and more particularly less than 0.2% and still more particularly less than 0.1% by weight relative to the total weight of the composition.

According to a particularly preferred embodiment, the composition according to the invention comprises at least one cationic surfactant, such as salts of optionally polyoxyalkylenated primary, secondary or tertiary fatty amines, quaternary ammonium salts, and mixtures thereof.

By way of quaternary ammonium salts, there may be mentioned in particular, for example:

those which have the following general formula (V):

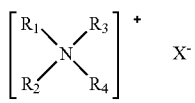
(V)

in which the symbols $R_1$ to $R_4$, which may be identical or different, represent a linear or branched aliphatic radical containing from 1 to 30 carbon atoms, or an aromatic radical such as aryl or alkylaryl. The aliphatic radicals may contain heteroatoms such as in particular oxygen, nitrogen, sulfur and halogens. The aliphatic radicals are for example selected from the group consisting of alkyl, alkoxy, $(C_2-C_6)$ polyoxyalkylene, alkylamide, $(C_{12}-C_{22})$alkylamido$(C_2-C_6)$alkyl, $(C_{12}-C_{22})$alkyl acetate, hydroxyalkyl, containing from about 1 to 30 carbon atoms; $X^-$ is an anion selected from the group consisting of the group comprising halides, phophates, acetates, lactates, $(C_2-C_6)$alkyl sulfates, alkyl or alkylaryl sulfonates;

the quaternary ammonium salts of imidazoline, such as for example those of the following formula (VI):

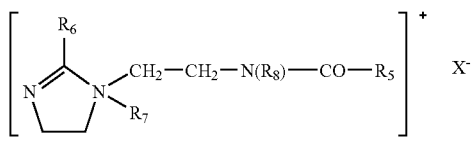
(VI)

in which $R_5$ represents an alkenyl or alkyl radical comprising from 8 to 30 carbon atoms, for example derived from tallow or coprah fatty acids, $R_6$ represents a hydrogen atom, a $C_1-C_4$ alkyl radical or an alkenyl or alkyl radical comprising from 8 to 30 carbon atoms, $R_7$ represents a $C_1-C_4$ alkyl radical, $R_8$ represents a hydrogen atom, a $C_1-C_4$ alkyl radical, X is an anion selected from the group consisting of the group comprising halides, phosphates, acetates, lactates, alkyl sulfates, alkyl or alkylaryl sulfonates. Preferably, $R_5$ and $R_6$ denote a mixture of alkenyl or alkyl radicals comprising from 12 to 21 carbon atoms, for example derived from tallow fatty acids, $R_7$ denotes methyl, $R_8$ denotes hydrogen. Such a product is, for example, Quaternium-27 (CTFA 1997) or Quaternium-83 (CTFA 1997) marketed under the names "REWOQUAT®" W 75, W90, W75PG, W75HPG by the company WITCO, the diquaternary ammonium salts of formula (VII):

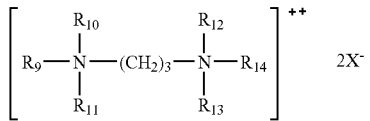
(VII)

in which $R_9$ denotes an aliphatic radical comprising about from 16 to 30 carbon atoms, $R_{10}$, $R_{11}$, $R_{12}$, $R_{13}$ and $R_{14}$, which are identical or different, are selected from the group consisting of hydrogen or an alkyl radical comprising from 1 to 4 carbon atoms, and $X^-$ is an anion selected from the group consisting of the group comprising halides, acetates, phosphates, nitrates, ethyl sulfates and methyl sulfates. Such, ethyl sulfates diquaternary ammonium salts optionally comprise propane tallow diammonium dichloride, the quaternary ammonium salts containing at least one ester functional group, such as those of the following formula (VIII):

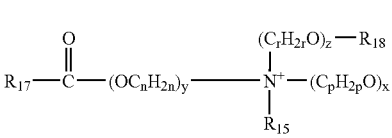
(VIII)

in which:

$R_{15}$ is selected from the group consisting of $C_1-C_6$ alkyl radicals and $C_1-C_6$ hydroxyalkyl or dihydroxyalkyl radicals;

$R_{16}$ is selected from the group consisting of:

the radical

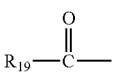

the saturated or unsaturated, linear or branched $C_1-C_{22}$ hydrocarbon radicals $R_{20}$, a hydrogen atom, $R_{17}$ is selected from the group consisting of:

the radical

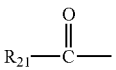

the saturated or unsaturated, linear or branched $C_1-C_6$ hydrocarbon radicals $R_{22}$, a hydrogen atom, $R_{17}$, $R_{19}$ and $R_{21}$, which are identical or different, are selected from the group consisting of saturated or unsaturated, linear or branched $C_7-C_{21}$ hydrocarbon radicals;

r, n and p which are identical or different, are integers ranging from 2 to 6;

y is an integer ranging from 1 to 10;

x and z, which are identical or different, are integers ranging from 0 to 10;

$X^-$ is a simple or complex, organic or inorganic anion; provided that x+y+z is equal to 1 to 15, that when x is equal to 0, then $R_{16}$ denotes $R_{20}$ and that when z is equal to 0 then $R_{18}$ denotes $R_{22}$.

The alkyl radicals $R_{15}$ may be linear or branched, and more particularly linear.

Preferably, $R_{15}$ denotes a methyl, ethyl, hydroxyethyl or dihydroxypropyl radical and more particularly a methyl or ethyl radical.

Advantageously, the sum x+y+z is equal to 1 to 10.

When $R_{16}$ is a hydrocarbon radical $R_{20}$, it may be long and may have from 12 to 22 carbon atoms, or may be short and may have from 1 to 3 carbon atoms.

When $R_{18}$ is a hydrocarbon radical $R_{22}$, it preferably has 1 to 3 carbon atoms. Advantageously $R_{17}$, $R_{19}$ and $R_{21}$, which are identical or different, are selected from the group consisting of saturated or unsaturated, linear or branched $C_{11}$-$C_{21}$ hydrocarbon radicals and more particularly from saturated or unsaturated, linear or branched $C_{11}$-$C_{21}$ alkyl and alkenyl radicals.

Preferably, x and z, which are identical or different, are equal to 0 or 1.

Advantageously, y is equal to 1.

Preferably, r, n and p, which are identical or different, are equal to 2 or 3, and still more particularly are equal to 2.

The anion $X^-$ is preferably a halide (chloride, bromide or iodide) or a (C1-C4)alkyl sulfate, more particularly methyl sulfate. It is possible, however, to use methanesulfonate, phosphate, nitrate, tosylate, an anion derived from an organic acid such as acetate or lactate or any other anion compatible with ammonium containing an ester functional group.

The anion $X^-$ is still more particularly chloride or methyl sulfate.

There are more particularly used in the composition according to the invention the ammonium salts of formula (IV) in which:

$R_{15}$ denotes a methyl or ethyl radical,
x and y are equal to 1;
z is equal to 0 or 1;
r, n and pt are equal to 2;
$R_{16}$ is selected from the group consisting of:
the radical

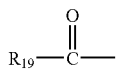

the methyl, ethyl or $C_{14}$-$C_{22}$ hydrocarbon radicals,
a hydrogen atom;
$R_{18}$ is selected from the group consisting of:
the radical

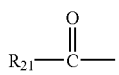

a hydrogen atom;
$R_{17}$, $R_{19}$ and $R_{21}$, which are identical or different, are selected from the group consisting of saturated or unsaturated, linear or branched $C_{13}$-$C_{17}$ hydrocarbon radicals, and preferably from saturated or unsaturated, linear or branched $C_{13}$-$C_{17}$ alkyl and alkenyl radicals.

Advantageously, the hydrocarbon radicals are linear.

There may be mentioned, for example, the compounds of formula (VIII) such as the salts (chloride or methyl sulfate in particular) of diacyloxyethyldimethylammonium, diacyloxyethylhydroxyethylmethylammonium, monoacyloxyethyldihydroxyethylmethylammonium, triacyloxyethylmethylammonium, monoacyloxyethylhydroxyethyldimethylammonium, and mixtures thereof. The acyl radicals preferably have 14 to 18 carbon atoms and are obtained more particularly from a vegetable oil such as palm or sunflower oil.

When the compound contains several acyl radicals they may be identical or different.

These products are obtained, for example, by direct esterification of triethanolamine, or triisopropanolamine, or alkyldiethanolamine or of alkyldiisopropanolamine optionally oxyalkylenated on the fatty acids or on mixtures of fatty acids of plant or animal origin, or by transesterification of their methyl esters. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol or glycerol chlorohydrin.

Such compounds are for example marketed under the names DEHYQUART® by the company COGNIS, STEPANQUAT® by the company STEPAN, NOXAMIUM® by the company CECA, REWOQUAT® WE 18 by the company REWO-GOLDSCHMIDT.

The composition according to the invention may preferably contain a mixture of quaternary ammonium mono-, di- and triester salts with a majority by weight of diester salts.

As a mixture of ammonium salts, it is possible to use for example the mixture containing 15 to 30% by weight of acyloxyethyldihydroxyethylmethylammonium methyl sulfate, 45 to 60% of diacyloxyethylhydroxyethylmethylammonium methyl sulfate, and 15 to 30% of triacyloxyethylmethylammonium methyl sulfate, the acyl radicals having from 14 to 18 carbon atoms and being obtained from optionally partially hydrogenated palm oil.

It is also possible to use the ammonium salts containing at least an ester functional group which are described in patents U.S. Pat. No. 4,874,554 and U.S. Pat. No. 4,137,180.

Among the quaternary ammonium salts mentioned above, the use of those corresponding to formula (V) is preferred. There may be mentioned in particular, on the one hand, tetraalkylammonium chlorides such as, for example, dialkyldimethylammonium or alkyltrimethylammonium chlorides in which the alkyl radical contains from about 12 to 22 carbon atoms, in particular behenyltrimethylammonium, distearyidimethylammonium, cetyltrimethylammonium, benzyldimethylstearylammonium chlorides or, on the other hand, palmitylamidopropyltrimethylammonium chloride or stearamidopropyidimethyl-(myristyl acetate)-ammonium chloride marketed under the name CERAPHYL® 70 by the company VAN DYK.

The cationic surfactants which are particularly preferred in the composition of the invention are selected from the group consisting of the quaternary ammonium salts, and in particular from behenyltrimethylammonium chloride, cetyltrimethylammonium chloride, quaternium-83, behenylamidopropyl(2,3-dihydroxypropyl)dimethylammonium chloride and palmitylamidopropyltrimethylammonium chloride.

Also, preferred cationic surfactants are cationic surfactants which are soluble in the composition and in particular those which are soluble in water, or those which are solubilized in water or in the composition with at least one nonionic surfactant.

The expression cationic surfactants which are soluble in water or the composition is understood to mean the cationic surfactants which are soluble in water or the composition at a concentration greater than or equal to 0.1% by weight in water at 25° C., that is to say that they form under these conditions a transparent solution which is macroscopically isotropic.

The composition according to the invention preferably contains the cationic surfactant(s) in a quantity ranging from 0.05 to 10% by weight, preferably from 0.1 to 5% by weight relative to the total weight of the composition.

According to a preferred embodiment, the compositions according to the invention may additionally comprise at least one cationic polymer, and preferably at least two cationic polymers which are different from each other.

The cationic polymers which can be used in accordance with the present invention may be selected from the group consisting of all those polymers already known in the art, especially those known to improve cosmetic properties, namely in particular those described in Patent Application EP-A- 0 337 354 and in French Patent Applications FR-A- 2 270 846, 2 383 660, 2 598 611, 2 470 596 and 2 519 863.

The preferred cationic polymers are selected from the group consisting of those which contain units containing primary, secondary, tertiary and/or quaternary amine groups which may form part of the main polymer chain, or which may be carried by a side substituent directly attached to it.

The cationic polymers used generally have a number-average molecular mass (molecular weight) between 500 and $5.10^6$ approximately, preferably between $10^3$ and $3.10^6$ approximately.

Among the cationic polymers, there may be mentioned more particularly the polymers of the polyamine, polyaminoamide and polyquaternary ammonium type. They are known products.

The polymers of the polyamine, polyamidoamide and polyquaternary ammonium type which can be used in accordance with the present invention, which may be especially mentioned, are those described in French Patents No. 2,505, 348 or 2,542,997. Among these polymers, there may be mentioned:

(1) the homopolymers or copolymers derived from acrylic or methacrylic esters or amides and comprising at least one of the units of the following formulae:

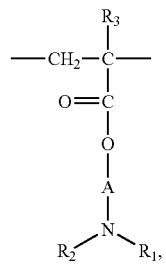
(IX)

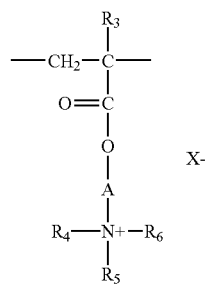
(X)

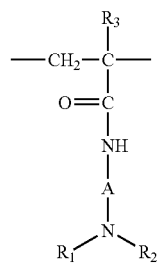
(XI)

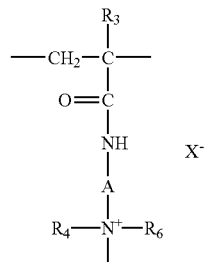
(XII)

in which:
$R_1$ and $R_2$, which are identical or different, represent hydrogen or an alkyl group having from 1 to 6 carbon atoms and preferably methyl or ethyl;
$R_3$, which are identical or different, denote a hydrogen atom or a $CH_3$ radical;
A, which are identical or different, represent a linear or branched alkyl group of 1 to 6 carbon atoms, preferably 2 or 3 carbon atoms or a hydroxyalkyl group of 1 to 4 carbon atoms;
$R_4$, $R_5$, $R_6$, which are identical or different, represent an alkyl group having from 1 to 18 carbon atoms or a benzyl radical and preferably an alkyl group having from 1 to 6 carbon atoms;
$X^-$ denotes an anion derived from an inorganic or organic acid such as a methyl sulfate or ethyl sulfate anion or a halide such as chloride or bromide.

The copolymers of the family (1) may contain, in addition, one or more units derived from comonomers which may be selected from the group consisting of the family of acrylamides, methacrylamides, diacetone acrylamides, acrylamides and methacrylamides substituted on the nitrogen with lower ($C_1$-$C_4$)alkyls, acrylic or methacrylic acids or esters thereof, vinyllactams such as vinylpyrrolidone or vinylcaprolactam, vinyl esters.

Thus, among these copolymers of the family (1), there may be mentioned:
the copolymers of acrylamide and dimethylaminoethyl methacrylate quaternized with dimethyl sulfate or with a dimethyl halide such as that sold under the name HERCOFLOC by the company HERCULES,
the copolymers of acrylamide and methacryloyloxyethyl-trimethylammonium chloride described, for example, in Patent Application EP-A-080976 and sold under the name BINA QUAT P 100 by the company CIBA,
the copolymer of acrylamide and methacryloyloxyethyltrimethylammonium methosulfate sold under the name RETEN by the company HERCULES,
the vinylpyrrolidone/dialkylaminoalkyl acrylate or methacrylate copolymers, quaternized or otherwise, such as the products sold under the name "GAFQUAT" by the company ISP such as for example "GAFQUAT® 734" or "GAFQUAT® 755" or alternatively the products called "COPOLYMER 845, 958 and 937". These polymers are described in detail in French patents 2,077,143 and 2,393,573,
the dimethylaminoethyl methacrylate/vinylcaprolactam/vinylpyrrolidone terpolymers such as the product sold under the name GAFFIX® VC 713 by the company ISP,
the vinylpyrrolidone/methacrylamidopropyldimethylamine copolymers marketed in particular under the name STYLEZE® CC 10 by ISP,
and the quaternized vinylpyrrolidone/dimethylaminopropyl methacrylamide copolymers such as the product sold under the name "GAFQUAT® HS 100" by the company ISP.

2) The cationic polysaccharides, in particular the cationic celluloses, starches and galactomannan gums. Among the cationic polysaccharides, there may be mentioned more particularly the cellulose ethers comprising quaternary ammonium groups, the cationic cellulose copolymers or the celluloses grafted with a quaternary ammonium water-soluble monomer and the cationic galactomannan gums.

The cellulose ethers comprising quaternary ammonium groups described in French Patent 1,492,597, and in particular the polymers marketed under the names "JR" (JR 400, JR 125, JR 30M) or "LR" (LR 400, LR 30M) by the company AMERCHOL. These polymers are also defined in the CTFA dictionary as hydroxyethyl cellulose quaternary ammoniums which have reacted with an epoxide substituted by a trimethylammonium group.

Cationic cellulose copolymers or celluloses grafted with a quaternary ammonium water-soluble monomer, are described especially in U.S. Pat. No. 4,131,576, such as hydroxyalkyl celluloses like hydroxymethyl, hydroxyethyl or hydroxypropyl celluloses grafted especially with a methacryloylethyltrimethylammonium, methacrylamidopropyltrimethylammonium or dimethyldiallylammonium salt.

The commercialized products corresponding to this definition are more particularly the products sold under the name "CELQUAT® L 200" and "CELQUAT® H 100" by the company NATIONAL STARCH.

Cationic galactomannan gums are described more particularly in U.S. Pat. Nos. 3,589,578 and 4,031,307 in particular the guar gums containing cationic trialkylammonium groups. Guar gums modified with a 2,3-epoxypropyltrimethylammonium salt (e.g. chloride) are for example used.

Such products are marketed in particular under the trade names JAGUAR® C13 S, JAGUAR® C 15, JAGUAR® C 17 or JAGUAR® C162 by the company RHODIA CHIMIE.

There also may be used starches modified with a 2,3-epoxypropyltrimethylammonium salt (e.g. chloride), such as for example the product called starch hydroxypropyltrimonium chloride according to the INCI nomenclature and marketed under the name SENSOMER Ci-50 from ONDEO.

(3) polymers consisting of piperazinyl units and of alkylene or hydroxyalkylene divalent radicals with straight or branched chains, optionally interrupted by oxygen, sulfur or nitrogen atoms or by aromatic or heterocyclic rings, as well as the oxidation and/or quaternization products of these polymers. Such polymers are described especially in French patents 2,162,025 and 2,280,361;

(4) water-soluble polyaminoamides prepared in particular by polycondensation of an acid compound with a polyamine; these polyaminoamides may be crosslinked with an epihalohydrin, a diepoxide, a dianhydride, an unsaturated dianhydride, a diunsaturated derivative, a bishalohydrin, a bisazetidinium, a bishaloacyidiamine, an alkyl bishalide or else with an oligomer resulting from the reaction of a difunctional compound which is reactive toward a bishalohydrin, a bisazetidinium, a bishaloacyldiamine, an alkyl bishalide, an epihalohydrin, a diepoxide or a diunsaturated derivative; the crosslinking agent being employed in proportions ranging from 0.025 to 0.35 mol per amine group of the polyaminoamide; these polyaminoamides may be alkylated or, if they include one or more tertiary amine functional groups, quaternized. Such polymers are described especially in French Patents 2,252,840 and 2,368,508, (5) polyaminoamides resulting from the condensation of polyalkylenepolyamines with polycarboxylic acids, followed by an alkylation with bifunctional agents. There may be mentioned, for example, the adipic acid-dialkylaminohydroxyalkyldialkylenetriamine polymers in which the alkyl radical contains from 1 to 4 carbon atoms and preferably denotes methyl, ethyl or propyl. Such polymers are described especially in French Patent 1,583,363.

Among these derivatives there may be mentioned more particularly the adipic acid/dimethylaminohydroxypropyl/diethylenetriamine polymers sold under the name "CARTARETINE® F, F4 or F8" by the company SANDOZ.

(6) polymers obtained by reaction of a polyalkylenepolyamine containing two primary amine groups and at least one secondary amine group with a dicarboxylic acid selected from the group consisting of diglycolic acid and saturated aliphatic dicarboxylic acids containing from 3 to 8 carbon atoms. The molar ratio of the polyalkylenepolyamine to the dicarboxylic acid being between 0.8:1 and 1.4:1; the polyaminoamide resulting therefrom being made to react with epichlorohydrin in a molar ratio of epichlorohydrin relative to the secondary amine group of the polyaminoamide of between 0.5:1 and 1.8:1. Such polymers are described especially in U.S. Pat. Nos. 3,227,615 and 2,961,347.

Polymers of this type are marketed in particular under the name "HERCOSETT® 57" by the company HERCULES INC. or else under the name of "PD 170" or "DELSETTE® 101" by the company HERCULES in the case of the copolymer of adipic acid/epoxypropyl/diethylenetriamine.

(7) cyclopolymers of alkyldiallylamine or of dialkyldiallylammonium, such as the homopolymers or copolymers comprising, as main constituent of the chain, units corresponding to the formulae (XIII) or (XIV):

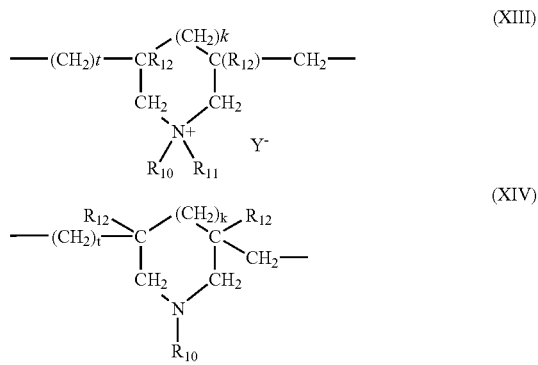

in which formulae k and t are equal to 0 or 1, the sum k+t being equal to 1; $R_{12}$ denotes a hydrogen atom or a methyl radical; $R_{10}$ and $R_{11}$, independently of each other, denote an alkyl group containing from 1 to 8 carbon atoms, a hydroxyalkyl group in which the alkyl group preferably has 1 to 5 carbon atoms, or a lower ($C_1$-$C_4$)amidoalkyl group or $R_{10}$ and $R_{11}$ may denote, jointly with the nitrogen atom to which they are attached, heterocyclic groups such as piperidinyl or morpholinyl; $Y^-$ is an anion such as bromide, chloride, acetate, borate, citrate, tartrate, bisulfate, bisulfite, sulfate or phosphate. These polymers are described especially in French Patent 2,080,759 and in its certificate of addition 2,190,406.

$R_{10}$ and $R_{11}$, independently of each other, preferably denote an alkyl group having from 1 to 4 carbon atoms.

Among the polymers defined above there may be mentioned more particularly the dimethyldiallylammonium chloride homopolymer sold under the name "MERQUAT® 100" by the company NALCO (and its homologues of low weight-average molecular masses) and the copolymers of diallyldimethylammonium chloride and acrylamide marketed under the name "MERQUAT® 550".

(8) The diquaternary ammonium polymer containing repeat units corresponding to the formula:

formula (XIV) in which:
$R_{13}$, $R_{14}$, $R_{15}$ and $R_{16}$, which are identical or different, represent aliphatic, alicyclic or arylaliphatic radicals containing from 1 to 20 carbon atoms or lower hydroxyalkylaliphatic radicals, or else $R_{13}$, $R_{14}$, $R_{15}$ and $R_{16}$, together or separately, form, with the nitrogen atoms to which they are attached, heterocyclic rings optionally containing a second heteroatom other than nitrogen, or else $R_{13}$, $R_{14}$, $R_{15}$ and $R_{16}$ represent a linear or branched $C_1$-$C_6$ alkyl radical substituted by a nitrile, ester, acyl, amide or —CO—O—$R_{17}$-D or —CO—NH—$R_{17}$-D group where $R_{17}$ is an alkylene and D a quaternary ammonium group;

$A_1$ and $B_1$ represent polymethylene groups containing from 2 to 20 carbon atoms which may be linear or branched, saturated or unsaturated and which may contain, bonded to or inserted into the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{13}$ and $R_{15}$, with the two nitrogen atoms to which they are attached, may form a piperazine ring; in addition if $A_1$ denotes a saturated or unsaturated, linear or branched alkylene or hydroxyalkylene radical, $B_1$ may also denote a group $(CH_2)_n$—CO-D-OC—$(CH_2)_n$— in which D denotes:

a) a glycol residue of formula: —O-Z-O—, where Z denotes a linear or branched hydrocarbon radical or a group corresponding to one of the following formulae:

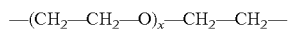

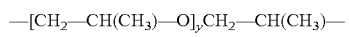

where x and y denote an integer from 1 to 4, representing a defined and unique degree of polymerization or any number from 1 to 4 representing a mean degree of polymerization;

b) a disecondary diamine residue such as a piperazine derivative;

c) a diprimary diamine residue of formula: —NH—Y—NH—, where Y denotes a linear or branched hydrocarbon radical or else the divalent radical

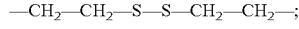

d) a ureylene group of formula: —NH—CO—NH—;

Preferably, $X^-$ is a monovalent inorganic or organic anion such as a halide (chloride, bromide), a sulfate, or a carboxylate (acetate, lactate, citrate).

These polymers have a number-average molecular mass (molecular weight) which is generally between 1000 and 100,000.

Polymers of this type are described especially in French Patents 2,320,330, 2,270,846, 2,316,271, 2,336,434 and 2,413,907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is possible to use more particularly the polymers which consist of repeat units corresponding to the formula:

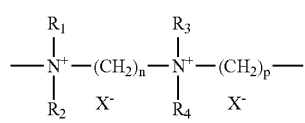

in which $R_1$, $R_2$, $R_3$ and $R_4$, which are identical or different, denote an alkyl or hydroxyalkyl radical having from 1 to 4 carbon atoms approximately, n and p are integers varying from 2 to 20 approximately and $X^-$ is an anion derived from an inorganic or organic acid.

An especially preferred compound of formula (XV) is that for which $R_1$, $R_2$, $R_3$ and $R_4$ represent a methyl radical and n=3, p=6 and X=Cl, called Hexadimethrine chloride according to the INCI nomenclature (CTFA).

(9) Polyquaternary ammonium polymers consisting of units of formula (XVI):

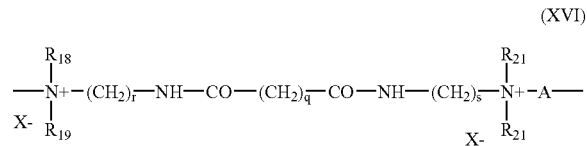

in which formula:

$R_{18}$, $R_{19}$, $R_{20}$ and $R_{21}$, which are identical or different, represent a hydrogen atom or a methyl, ethyl, propyl, β-hydroxyethyl, β-hydroxypropyl or —$CH_2CH_2(OCH_2CH_2)_p$OH radical, where p is equal to 0 or to an integer between 1 and 6, provided that $R_{18}$, $R_{19}$, $R_{20}$ and $R_{21}$ do not simultaneously denote a hydrogen atom, r and s, which are identical or different, are integers between 1 and 6, q is equal to 0 or to an integer between 1 and 34, $X^-$ denotes an anion such as a halide, A denotes a radical of a dihalide or preferably represents —$CH_2$—$CH_2$—O—$CH_2$—$CH_2$—.

Such compounds are described especially in Patent Application EP-A-122 324.

Among these there may be mentioned, for example, the products "MIRAPOL® A 15", "MIRAPOL® AD1", "MIRAPOL® AZ1" and "MIRAPOLO 175", sold by the company MIRANOL.

(10) Quaternary vinylpyrrolidone and vinylimidazole polymers such as polyquaternium-11, polyquaternium-16, polyquaternium-44, in particular the products marketed under the names LUVIQUAT® FC 905, FC 550 and FC 370 and LUVIQUAT® CARE by the company B.A.S.F.

(11) Polyamines like POLYQUART® H sold by COGNIS, referred to under the name of "POLYETHYLENE GLYCOL (15) TALLOW POLYAMINE" in the CTFA dictionary.

(12) The crosslinked or noncrosslinked polymers of methacryloyloxy($C_1$-$C_4$ alkyl)tri($C_1$-$C_4$ alkyl)ammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. More particularly, it is possible to employ a crosslinked acrylamide/methacryloyloxyethyltrimethylammonium chloride copolymer (20/80 by weight) in the form of a dispersion containing 50% by weight of said copolymer in mineral oil.

This dispersion is marketed under the name of "SALCARE® SC 92" by the company CIBA. It is also possible to employ a crosslinked methacryloyloxyethyltrimethylammonium chloride homopolymer containing approximately 50% by weight of the homopolymer in mineral oil or in a liquid ester. These dispersions are marketed under the names of "SALCARE® SC 95" and "SALCARE® SC 96" by the company CIBA.

Other cationic polymers that may be employed within the scope of the invention include cationic proteins or hydrolyzates of cationic proteins, polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers capable of being used within the scope of the present invention, it is preferable to use quaternary cellulose ether derivatives such as the products sold under the name "JR 400" by the company AMERCHOL, cationic cyclopolymers, in particular the homopolymers or copolymers of dimethyldiallylammonium chloride, sold under the names "MERQUAT® 100", "MERQUAT® 550" and "MERQUAT® S" by the company NALCO, copolymers of vinylpyrrolidone and of salts (e.g. methyl sulfate or ethyl sulfate) of methylvinylimidazolium which are sold in particular under the name LUVIQUAT CARE by BASF, and mixtures thereof.

According to the invention, the composition preferably comprises at least one cationic polysaccharide and at least one quaternary polymer of vinylpyrrolidone and vinylimidazole.

According to the invention, the composition preferably comprises at least one homopolymer of diallyldimethylammonium chloride and at least one quaternary polymer of vinylpyrrolidone and vinylimidazole.

According to the invention, each cationic polymer may preferably represent from 0.001% to 20% by weight, more preferably from 0.01% to 10% by weight, and even more particularly from 0.05 to 2% by weight relative to the total weight of the final composition.

According to a preferred embodiment of the invention, the compositions according to the invention may comprise at least one thickener. This thickener is preferably nonionic.

The nonionic thickeners according to the invention may be of natural or synthetic origin. They are chosen in particular from:
(i) nonionic homopolymers and copolymers containing ethylenically unsaturated monomers of the ester and/or amide type,
(ii) homo- or copolymers of vinylpyrrolidone,
(iii) polysaccharides.

Among the nonionic homopolymers or copolymers containing ethylenically unsaturated monomers of the ester and/or amide type, there may particularly be mentioned polyamides, in particular the products sold under the names: CYANAMER P250 by the company CYTEC (polyacrylamide); methyl methacrylate/ethylene glycol dimethacrylate copolymers (PMMA MBX-8C by the company US COSMETICS); butyl methacrylate/methyl methacrylate copolymers (ACRYLOID B66 by the company RHOM & HMS), polymethyl methacrylates (BPA 500 by the company KOBO).

The homo- or copolymers of vinylpyrrolidone are chosen in particular from crosslinked homopolymers of vinylpyrrolidone such as POLYMER ACP-10 marketed by ISP.

The thickening polysaccharides are chosen in particular from glucans, modified or unmodified starches (such as those derived, for example, from cereals such as wheat, corn or rice, vegetables such as golden pea, tubers such as potato or cassava), amylose, amylopectin, glycogen, dextrans, celluloses and derivatives thereof (methylcelluloses, hydroxyalkylcelluloses, ethylhydroxyethylcelluloses), mannans, xylans, lignins, arabans, galactans, galacturonans, chitin, chitosans, glucoronoxylans, arabinoxylans, xyloglucans, glucomannans, pectic acids and pectins, arabinogalactans, carrageenans, agars, gums arabic, gums tragacanth, Ghatti gums, Karaya gums, carob gums, galactomannans such as guar gums and their nonionic derivatives (hydroxypropylguar), and mixtures thereof.

In general, the compounds of this type, which can be used in the present invention, are selected from the group consisting of those which are described in particular in "Encyclopedia of Chemical Technology, Kirk-Othmer, Third Edition, 1982, volume 3, pp. 896-900, and volume 15, pp 439-458", in "Polymers in Nature, by E. A. MacGREGOR and C. T. GREENWOOD, Editions John Wiley & Sons, Chapter 6, pp 240-328, 1980" and in "Industrial Gums—Polysaccharides and their Derivatives, published by Roy L. WHISTLER, Second Edition, Edition Academic Press Inc.", the content of these three books being completely incorporated into the present application by way of reference.

Starches, guar gums, celluloses and derivatives thereof will be preferably used.

The polysaccharides may be modified or unmodified.

The unmodified guar gums are for example the products sold under the name VIDOGUM GH 175 by the company UNIPECTINE, and under the names MEYPRO-GUAR 50 and JAGUAR C by the company RHODIA CHIMIE.

The modified nonionic guar gums are in particular modified with $C_1$-$C_6$ hydroxyalkyl groups.

Among the hydroxyalkyl groups, there may be mentioned, by way of example, the hydroxymethyl, hydroxyethyl, hydroxypropyl and hydroxybutyl groups.

These guar gums are well known in the state of the art and may, for example, be prepared by reacting the corresponding alkene oxides, such as for example propylene oxides, with guar gum so as to obtain a guar gum modified with hydroxypropyl groups.

The hydroxyalkylation ratio, which corresponds to the number of alkylene oxide molecules consumed to the number of free hydroxyl functional groups present on the guar gum, preferably varies from 0.4 to 1.2.

Such nonionic guar gums, optionally modified with hydroxyalkyl groups, are for example sold under the trade names JAGUAR HP8, JAGUAR HP60 and JAGUAR HP120, JAGUAR DC 293 and JAGUAR HP 105 by the company RHODIA CHIMIE (RHODIA CHIMIE) or under the name GALACTASOL 4H4FD2 by the company AQUALON.

Among the celluloses, hydroxyethylcelluloses and hydroxypropylcelluloses are in particular used. The products sold under the names KLUCEL EF, KLUCEL H, KLUCEL LHF, KLUCEL MF, KLUCEL G, by the company AQUALON, CELLOSIZE POLYMER PCG-10 by the company AMERCHOL, may be mentioned.

Preferably, the thickening agents of the cosmetic compositions in accordance with the present invention advantageously have, in solution or in dispersion, at 1% active substance in water, a viscosity, measured by means of a Brookfield viscometer at a shear rate of 20 rpm, greater than 5 mPa/s, and still more advantageously greater than 10 mPa/s.

According to the invention, the thickening agent(s) may represent from 0.001% to 20% by weight, preferably from 0.01% to 10% by weight, and more particularly from 0.1 to 3% by weight relative to the total weight of the final composition.

The composition according to the invention may optionally contain surfactants other than cationic surfactants.

The surfactants which can be used in the present invention may be selected from the group consisting of conventional anionic, nonionic and amphoteric surfactants well known in the art, and mixtures thereof.

The compositions of the invention advantageously additionally contain at least one surfactant selected from the group consisting of anionic, amphoteric and nonionic surfactants, or mixtures thereof, which is generally present in a quantity between 0.1% and 60% by weight approximately, preferably between 3% and 40%, and still more preferably between 5% and 30%, relative to the total weight of the composition.

The surfactants which are suitable for carrying out the present invention are especially the following:

(i) Anionic Surfactant(s):

Their nature is not of truly critical importance within the context of the present invention.

Thus, by way of example of anionic surfactants that can be employed, by themselves or as mixtures, in the context of the present invention, there may be mentioned especially (nonlimiting list) the salts (in particular alkali metal, especially sodium, salts, ammonium salts, amine salts, aminoalcohol salts or magnesium salts) of the following compounds: alkyl sulfates, alkyl ether sulfates, alkylamido ether sulfates, alkylaryl polyether sulfates, monoglyceride sulfates, alkyl sulfonates, alkyl phosphates, alkylamidesulfonates, alkyl aryl sulfonates, α-olefinsulfonates, paraffinsulfonates, alkyl sulfosuccinates, alkyl ether sulfosuccinates, alkylamidesulfosuccinates, alkyl sulfosuccinamates, alkyl sulfoacetates, alkyl ether phosphates, acyl sarcosinates, acyl isethionates and N-acyltaurates, the alkyl or acyl radical of all these different compounds preferably containing from 8 to 24 carbon atoms, and the aryl radical preferably denoting a phenyl or benzyl group. Among the anionic surfactants which are further usable there may also be mentioned the salts of fatty acids such as the salts of oleic, ricinoleic, palmitic and stearic acids, the acids of copra oil or of hydrogenated copra oil, and acyl lactylates in which the acyl radical contains 8 to 20 carbon atoms. It is also possible to employ weakly anionic surfactants, like alkyl-D-galactosideuronic acids and salts thereof, as well as the polyoxyalkylenated carboxylic ($C_6$-$C_{24}$)alkyl ether acids, the polyoxyalkylenated carboxylic ($C_6$-$C_{24}$)alkylaryl ether acids, the polyoxyalkylenated carboxylic ($C_6$-$C_{24}$) alkyl amidoether acids and their salts, in particular those containing from 2 to 50 ethylene oxide groups, and mixtures thereof. Among the anionic surfactants, the use of the salts of alkyl sulfates and of alkyl ether sulfates and mixtures thereof is preferred according to the invention.

(ii) Nonionic Surfactant(s):

The nonionic surfactants themselves are also compounds which are well known per se (in this respect see especially the "Handbook of Surfactants" by M. R. Porter, published by Blackie & Son (Glasgow and London), 1991, pp. 116-178) and, in the context of the present invention, their nature is not of critical importance. They can thus be chosen especially from (nonlimiting list) alcohols, alpha-diols, alkylphenols or polyethoxylated, polypropoxylated or polyglycerolated fatty acids which have a fatty chain containing, for example, 8 to 18 carbon atoms, it being possible for the number of ethylene oxide or propylene oxide groups to range especially from 2 to 50 and it being possible for the number of glycerol groups to range especially from 2 to 30. The copolymers of ethylene oxide and propylene oxide and the condensates of ethylene oxide and propylene oxide with fatty alcohols may also be mentioned; the polyethoxylated fatty amides preferably containing from 2 to 30 mol of ethylene oxide, the polyglycerolated fatty amides on average containing 1 to 5 glycerol groups and in particular 1.5 to 4; the oxyethylenated fatty acid esters of sorbitan containing from 2 to 30 mol of ethylene oxide, the fatty acid esters of sucrose, the fatty acid esters of polyethylene glycol, alkylpolyglycosides, the N-alkylglucamine derivatives, amine oxides such as the oxides of ($C_{10}$-$C_{14}$) alkylamines or the N-acylaminopropylmorpholine oxides. It will be noted that alkylpolyglycosides constitute nonionic surfactants which are particularly well suited within the context of the present invention.

(iii) Amphoteric Surfactant(s):

The amphoteric surfactants, the nature of which is not of critical importance in the context of the present invention, may be especially (nonlimiting list) derivatives of aliphatic secondary or tertiary amines in which the aliphatic radical is a linear or branched chain containing 8 to 22 carbon atoms and containing at least one water-solubilizing anionic group (for example carboxylate, sulfonate, sulfate, phosphate or phosphonate); ($C_8$-$C_{20}$)alkylbetaines, sulfobetaines, ($C_8$-$C_{20}$)alkylamido($C_1$-$C_6$)alkylbetaines or ($C_8$-$C_{20}$)alkylamido ($C_1$-$C_6$)alkylsulfobetaines may further be mentioned.

Among the amine derivatives there may be mentioned the products sold under the name MIRANOL, as described in U.S. Pat. Nos. 2,528,378 and 2,781,354 and of structures:

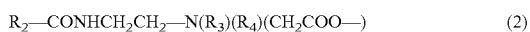

$$R_2-CONHCH_2CH_2-N(R_3)(R_4)(CH_2COO-) \qquad (2)$$

in which: $R_2$ denotes an alkyl radical derived from an acid $R_2$—COOH present in hydrolyzed copra oil, a heptyl, nonyl or undecyl radical, $R_3$ denotes a beta-hydroxyethyl group and $R_4$ a carboxymethyl group; and

$$R_5-CONHCH_2CH_2-N(B)(C) \qquad (3)$$

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the radical —$CH_2$—CHOH—$SO_3H$, $R_5$ denotes an alkyl radical of an acid $R_9$—COOH present in copra oil or in hydrolyzed linseed oil, an alkyl radical, especially $C_7$, $C_9$, $C_{11}$ or $C_{13}$, a $C_{17}$ alkyl radical and its iso form or an unsaturated radical $C_{17}$.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid, Cocoamphodipropionic acid.

By way of example, there may be mentioned the cocoamphodiacetate marketed under the trade name MIRANOL C2M concentrate by the company RHODIA CHIMIE.

In the compositions in accordance with the invention, use is preferably made of mixtures of surfactants and in particular mixtures of anionic surfactants and mixtures of anionic surfactants and amphoteric or nonionic surfactants. A particularly preferred mixture is a mixture consisting of at least one anionic surfactant and at least one amphoteric surfactant.

Use is preferably made of an anionic surfactant selected from the group consisting of sodium, triethanolamine or ammonium ($C_{12}$-$C_{14}$)alkyl sulfates, sodium, triethanolamine or ammonium ($C_{12}$-$C_{14}$)alkyl ether sulfates oxyethylenated with 2.2 mol of ethylene oxide, sodium cocoyl isethionate and sodium ($C_{14}$-$C_{16}$)alpha-olefin sulfonates and mixtures thereof with:

either an amphoteric surfactant such as the amine derivatives called disodium cocoamphodipropionate or sodium cocoamphopropionate marketed in particular by the company RHODIA CHIMIE under the trade name "MIRANOL C2M CONC" as an aqueous solution containing 38% active substance or under the name MIRANOL C32;

or an amphoteric surfactant such as alkylbetaines, in particular the cocobetaine marketed under the name "DEHYTON® AB 30" as an aqueous solution containing 32% AS by the company COGNIS or such as the ($C_8$-$C_{20}$)alkylamido-($C_1$-$C_6$)alkylbetaines, in particular TEGOBETAINE® F 50 marketed by the company GOLDSCHMIDT.

The composition according to the invention may additionally comprise at least one conditioner selected from the group consisting of silicones different from silicones with a quaternary ammonium group, the carboxylic esters comprising at least 12 carbon atoms, vegetable oils, mineral oils, synthetic oils such as poly(alpha-olefins), and mixtures thereof.

The silicones which can be used in accordance with the invention may be soluble or insoluble in the composition, and they may be in particular polyorganosiloxanes which are insoluble in the composition of the invention. They may be provided in the form of oils, waxes, resins or gums. They may be used pure or as an emulsion, as a dispersion or as a microemulsion.

The organopolysiloxanes are defined in greater detail in the book by Walter NOLL "Chemistry and Technology of Silicones" (1968) Academie Press. They may be volatile or nonvolatile.

When they are volatile, the silicones are more particularly selected from the group consisting of those possessing a boiling point of between 60° C. and 260° C., and more particularly still from:

(i) cyclic silicones comprising from 3 to 7 silicon atoms, and preferably 4 to 5. They are, for example, the octamethylcyclotetrasiloxane marketed in particular under the name "VOLATILE SILICONE 7207" by UNION CARBIDE or "SILBIONE 70045 V 2" by RHODIA, the decamethylcyclopentasiloxane marketed under the name "VOLATILE SILICONE 7158" by UNION CARBIDE, "SILBIONE 70045 V 5" by RHODIA, and mixtures thereof.

There may also be mentioned cyclocopolymers of the dimethylsiloxane/methylalkylsiloxane type, such as the "SILICONE VOLATILE FZ 3109" marketed by the company UNION CARBIDE, having the chemical structure:

with D:

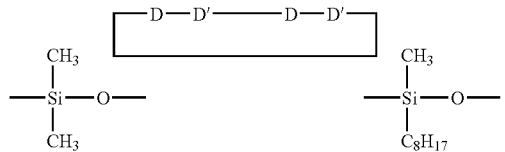

with D':

There may also be mentioned mixtures of cyclic silicones with organic compounds derived from silicon, such as the mixture of octamethylcyclotetrasiloxane and tetratrimethylsilylpentaerythritol (50/50) and the mixture of octamethylcyclotetrasiloxane and 1,1'-oxy(2,2,2',2',3,3'-hexatrimethylsilyloxy) bisneopentane;

(ii) linear volatile silicones having 2 to 9 silicon atoms and possessing a viscosity of less than or equal to $5\times10^{-6}$ $m^2$/s at 25° C. It is for example the decamethyltetrasiloxane marketed in particular under the name "SH 200" by the company TORAY SILICONE. Silicones entering into this class are also described in the article published in Cosmetics and toiletries, Vol. 91, Jan. 76, p. 27-32—TODD & BYERS "Volatile Silicone fluids for cosmetics".

Among the nonvolatile silicones, there may be mentioned in particular polyalkylsiloxanes, polyarylsiloxanes, polyalkylarylsiloxanes, silicone gums and resins, polyorganosiloxanes modified by organofunctional groups and mixtures thereof.

The organomodified silicones which can be used in accordance with the invention are silicones as defined above and comprising in their structure one or more organofunctional groups attached via a hydrocarbon group.

Among the organomodified silicones, there may be mentioned the polyorganosiloxanes comprising:

polyethyleneoxy and/or polypropyleneoxy groups optionally comprising $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the ($C_{12}$)alkyl methicone copolyol marketed by the company DOW CORNING under the name Q2 5200;

substituted or unsubstituted amine-containing groups such as the products marketed under the name GP 4 Silicone Fluid and GP 7100 by the company GENESEE or the products marketed under the names Q2 8220 and DOW CORNING 929 or 939 by the company DOW CORNING. The substituted amine-containing groups are in particular $C_1$-$C_4$ aminoalkyl groups;

thiol groups, such as the products marketed under the names "GP 72 A" and "GP 71" from GENESEE;

alkoxylated groups, such as the product marketed under the name "SILICONE COPOLYMER F-755" by SWS SILICONES and ABIL WAX® 2428, 2434 and 2440 by the company GOLDSCHMIDT;

hydroxylated groups, such as the polyorganosiloxanes with a hydroxyalkyl functional group which are described in French patent application FR-A-85 16334;

acyloxyalkyl groups such as, for example, the polyorganosiloxanes described in patent U.S. Pat. No. 4,957,732;

anionic groups of the carboxylic type, such as, for example, in the products described in patent EP 186 507 from the company CHISSO CORPORATION, or of the alkylcarboxylic type such as those present in the product X-22-3701$^E$ from the company SHIN-ETSU; 2-hydroxyalkylsulfonate; 2-hydroxyalkylthiosulfate such as the products marketed by the company GOLDSCHMIDT under the names "ABIL® S201" and "ABIL® S255";

hydroxyacylamino groups, such as the polyorganosiloxanes described in application EP 342 834. There may be mentioned, for example, the product Q2-8413 from the company DOW CORNING.

By way of examples of silicones, polydimethylsiloxanes, polyalkylarylsiloxanes and polydimethylsiloxanes with amino or alkoxylated groups are preferably used.

The composition according to the invention may also comprise one or more carboxylic acid esters such as, for example, the compounds of formula $R_aCOOR_b$ in which $R_a$ represents the residue of a higher fatty acid containing from 4 to 29 carbon atoms and $R_b$ represents a hydrocarbon chain containing from 3 to 30 carbon atoms, such as Purcellin oil (stearyl octanoate), ispropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, isostearyl neopentanoate and mixtures thereof.

The composition according to the invention may also comprise one or more vegetable oils such as sweet almond oil, avocado oil, castor oil, olive oil, jojoba oil, sunflower oil, wheatgerm oil, sesame oil, peanut oil, grapeseed oil, soybean oil, rapeseed oil, safflower oil, copra oil, corn oil, hazelnut oil, shea butter, palm oil, apricot stone oil, calophyllum oil and mixtures thereof.

As mineral oils, paraffin oil and liquid paraffin may be mentioned in particular.

The conditioners, which may be selected from the group consisting of silicones, esters, vegetable oils, mineral oils, synthetic oils and mixtures thereof, are preferably contained in the composition according to the invention in a quantity ranging from 0.01% to 20% by weight, even better ranging from 0.1% to 10% by weight, and more particularly ranging from 0.3% to 5% by weight relative to the total weight of the composition.

The cosmetically acceptable medium is preferably aqueous and may comprise water or a mixture of water and a cosmetically acceptable solvent such as a $C_1$-$C_4$ lower alcohol, for example ethanol, isopropanol, tert-butanol, n-butanol; polyols such as propylene glycol; polyol ethers; $C_5$-$C_{10}$ alkanes; acetone, methyl ethyl ketone; $C_1$-$C_4$ alkyl acetates such as methyl acetate, ethyl acetate, butyl acetate; dimethoxyethane, diethoxyethane; and mixtures thereof.

The cosmetically acceptable, in particular aqueous, medium preferably represents from 30 to 98% by weight relative to the total weight of the composition.

The pH of the compositions of the invention is preferably between 2 and 8, more preferably between 3 and 7.

According to the invention, the compositions are preferably transparent.

The transparency may be measured by the turbidity in a HACH—model 2100 P turbidimeter at 25° C. (the apparatus is standardized with formazin). The turbidity of the compositions according to the invention (in the absence of additional insoluble compounds) is then generally between 0.05 and 500 NTU and preferably between 10 and 300 NTU.

The compositions according to the invention may also contain conventional additives well known in the art, such as anionic, nonionic or amphoteric polymers, nonpolymeric thickeners such as acids or electrolytes, opacifiers, pearlescent agents, vitamins, provitamins such as panthenol, waxes such as vegetable waxes, natural or synthetic ceramides, perfumes, colorants, organic or inorganic particles, preservatives, pH stabilizing agents.

Persons skilled in the art know how to choose the possible additives and their quantity so that they do not adversely affect the properties of the compositions of the present invention in view of this disclosure.

These additives are generally present in the composition according to the invention in a quantity ranging from 0 to 20% by weight relative to the total weight of the composition.

The compositions of the invention may be provided in any form including in the form of a shampoo, a rinse-out or leave-in after-shampoo, compositions for permanent waving, hair straightening, dyeing or bleaching, or in the form of rinse-out compositions to be applied before or after dyeing, bleaching, permanent waving or hair straightening or between the two stages of a permanent waving or a hair straightening.

They can be used, for example, as after-shampoos, rinse-out treatments, deep treatment masks, treatment lotions or creams for the scalp.

According to a preferred embodiment of the invention, the composition may be used as a rinse-out after-shampoo, in particular on fine hair.

The (cosmetic) compositions according to the invention may also be provided in the form of a gel, milk, cream, emulsion, fluid or thickened lotions or mousse and may be used for the skin, the nails, the eyelashes, the lips and more particularly the hair.

The compositions may be packaged in various forms, in particular in vaporizers, pump dispensers or in aerosol containers in order to ensure application of the composition in vaporized form or in the form of a mousse. Such packaging forms are recommended, for example, when it is desired to obtain a spray, a lacquer or a mousse for the treatment of hair.

The present invention also relates to a method for the (cosmetic) treatment of keratinous materials such as, for example, the skin or the hair, which comprises in applying an effective quantity of a (cosmetic) composition as described above, to the keratinous materials, in optionally rinsing after an optional leave-in time. The rinsing is carried out for example with water.

Thus, this method according to the invention allows retention of the hairstyle, the treatment, care or washing of or the removal of make-up from the skin, the hair or any other keratinous material.

The following examples illustrate the present invention and should not be considered in any manner as limiting the invention.

EXAMPLE 1

The following rinse-out after-shampoo composition was prepared:

| | |
|---|---|
| Cetyltrimethylammonium chloride (DEHYQUART A OR from COGNIS) | 0.8 g AS |
| Quaternium-80 as a solution containing 50% AS in propylene glycol (ABIL QUAT 3272 from GOLDSCHMIDT) | 0.5 g AS |
| Oleyl alcohol | 0.25 g |
| Hydroxypropylguar (JAGUAR HP 105 from RHODIA CHIMIE) | 0.4 g |
| Polyquaternium-10 (JR400 from RHODIA CHIMIE) | 0.5 g |
| Polyquaternium-44 (LUVIQUAT CARE from BASF) | 0.57 g AS |
| Hydroxyethylcellulose (CELLOSIZE POLYMER PCG-10 from UNION CARBIDE) | 0.3 g |
| Glycerin | 5 g |
| Citric acid | 0.5 g |
| Perfume | qs |
| Preservatives | qs |
| Water qs | 100 g |

Water at room temperature is introduced into a manufacturing tank and then the preservatives and the polyquaternium-10 are added. The mixture is homogenized until complete dissolution is obtained. The hydroxypropylguar, the hydroxyethylcellulose previously dispersed in glycerin, and then the citric acid, the cetyltrimethylammonium chloride, the polyquaternium-44 and the quaternium-80 are then successively added.

When the mixture is homogeneous, the perfume is added.

The composition was applied for 1 to 5 minutes to hair which has been washed and wrung. The hair was then rinsed and dried.

The wet hair is then smooth and supple and the dried hair is supple and individualized.

EXAMPLE 2

The following rinse-out after-shampoo composition was prepared:

| | |
|---|---|
| Cetyltrimethylammonium chloride (DEHYQUART A OR from COGNIS) | 0.8 g AS |
| Quaternium-80 as a solution containing 50% AS in propylene glycol (ABIL QUAT 3272 from GOLDSCHMIDT) | 0.5 g AS |
| Isostearyl alcohol | 0.25 g |
| Hydroxypropylguar (JAGUAR HP 105 from RHODIA CHIMIE) | 0.4 g |
| Polyquaternium-10 (JR400 from RHODIA CHIMIE) | 0.5 g |
| Polyquaternium-44 (LUVIQUAT CARE from BASF) | 0.57 g AS |
| Hydroxyethylcellulose (CELLOSIZE POLYMER PCG-10 from UNION CARBIDE) | 0.3 g |
| Glycerin | 5 g |
| Citric acid | 0.5 g |
| Perfume | qs |
| Preservatives | qs |
| Water qs | 100 g |

The composition was applied for 1 to 5 minutes to hair which has been washed and wrung. The hair was then rinsed and dried.

The wet hair is then smooth and supple and the dried hair is supple and individualized.

EXAMPLE 3

The following rinse-out after-shampoo composition was prepared:

| | |
|---|---|
| Cetyltrimethylammonium chloride (DEHYQUART A OR from COGNIS) | 0.8 g AS |
| Quaternium-80 as a solution containing 50% AS in propylene glycol (ABIL QUAT 3272 from GOLDSCHMIDT) | 0.5 g AS |
| Oxyethylenated linear lauryl alcohol containing 4 mol of ethylene oxide | 0.25 g |
| Hydroxypropylguar (JAGUAR HP 105 from RHODIA CHIMIE) | 0.4 g |
| Behenyltrimethylammonium chloride (VARISOFT BT 85 from GOLDSCHMIDT) | 0.8 g AS |
| Decylglucoside as an aqueous solution containing 60% AS (ORAMIX CG 110 from SEPPIC) | 1.8 g AS |
| Polyquaternium-10 (JR400 from RHODIA CHIMIE) | 0.5 g |
| Polyquaternium-44 (LUVIQUAT CARE from BASF) | 0.57 g AS |
| Hydroxyethylcellulose (CELLOSIZE POLYMER PCG-10 from UNION CARBIDE) | 0.3 g |
| Glycerin | 5 g |
| Citric acid | 0.5 g |
| Perfume | qs |
| Preservatives | qs |
| Water qs | 100 g |

The composition was applied for 1 to 5 minutes to hair which has been washed and wrung. The hair was then rinsed and dried.

The wet hair is then smooth and supple and the dried hair is supple and individualized.

EXAMPLE 4

The following rinse-out after-shampoo composition was prepared:

| | |
|---|---|
| Cetyltrimethylammonium chloride (DEHYQUART A OR from COGNIS) | 0.8 g AS |
| Quaternium-80 as a solution containing 50% AS in propylene glycol (ABIL QUAT 3272 from GOLDSCHMIDT) | 0.5 g AS |
| Oxyethylenated linear lauryl alcohol containing 4 mol of ethylene oxide | 0.25 g |
| Hydroxypropylguar (JAGUAR HP 105 from RHODIA CHIMIE) | 0.6 g |
| Behenyltrimethylammonium chloride (VARISOFT BT 85 from GOLDSCHMIDT) | 0.8 g AS |
| Decylglucoside as an aqueous solution containing 60% AS (ORAMIX CG 110 from SEPPIC) | 1.8 g AS |
| Polyquaternium-44 (LUVIQUAT CARE from BASF) | 0.57 g AS |
| Hydroxyethylcellulose (CELLOSIZE POLYMER PCG-10 from UNION CARBIDE) | 0.3 g |
| Glycerin | 5 g |
| Citric acid | 0.5 g |
| Perfume | qs |
| Preservatives | qs |
| Water qs | 100 g |

The composition was applied for 1 to 5 minutes to hair which has been washed and wrung. The hair was then rinsed and dried.

The wet hair is then smooth and supple and the dried hair is supple and individualized.

EXAMPLE 5

The following rinse-out after-shampoo composition was prepared:

| | |
|---|---|
| Cetyltrimethylammonium chloride (DEHYQUART A OR from COGNIS) | 0.8 g AS |
| Quaternium-80 as a solution containing 50% AS in propylene glycol (ABIL QUAT 3272 from GOLDSCHMIDT) | 0.5 g AS |
| Oxyethylenated linear lauryl alcohol containing 4 mol of ethylene oxide | 0.25 g |
| Hydroxypropylguar (JAGUAR HP 105 from RHODIA CHIMIE) | 0.6 g |
| Polyquaternium-44 (LUVIQUAT CARE from BASF) | 0.57 g AS |
| Hydroxyethylcellulose (CELLOSIZE POLYMER PCG-10 from UNION CARBIDE) | 0.3 g |
| Glycerin | 5 g |
| Citric acid | 0.5 g |
| Perfume | Qs |
| Preservatives | Qs |
| Water qs | 100 g |

The composition was applied for 1 to 5 minutes to hair which has been washed and wrung. The hair was then rinsed and dried.

The wet hair is then smooth and supple and the dried hair is shiny, supple and individualized.

As used herein, the terms "about" and "approximately" preferably mean +/− 10%. The phrases "between X and Y" and "ranging from X to Y" include X and Y.

The above description of the invention sets forth the manner and process of making and using it such that it enables any person skilled in this art to make and use the same, specifically including the making and using of the following preferred embodiments and those set out in the claims, all of which make up a part of this description:

a (cosmetic) composition comprising, in a (cosmetically acceptable) medium, at least one silicone with quaternary ammonium groups and at least one liquid fatty alcohol: and methods of using the invention compositions to treat hair, skin, etc.

All references, documents, brochures, texts, articles, patents, applications, etc. mentioned above are incorporated herein by reference. All available literature for those commercially available materials mentioned herein is also incorporated herein by reference. Where a numerical limit or range is stated all endpoints are included, and all values and subranges within the stated ranges or limits are expressly included as if specifically written out.

The invention claimed is:

1. A transparent composition having a turbidity of between 10 and 300 NTU comprising, in a cosmetically acceptable medium, at least one silicone with quaternary ammonium groups represented by formula (III):

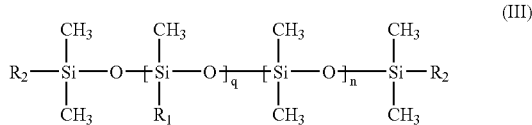

in which:

$R_1$, which is identical or different, represents a linear or branched $C_1$-$C_{30}$ alkyl group or phenyl group;

$R_2$, which is identical or different, represents —$C_cH_{2c}$—O—$(C_2H_4O)_a$—$(C_3H_6O)_b$—$R_5$ or —$C_cH_{2c}$—O—$(C_4H_8O)_a$—$R_5$;

$R_5$, which is identical or different, is selected from the group consisting of the groups of the following formula:

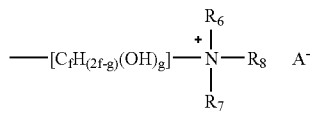

the radicals $R_8$ independently represent a linear or branched $C_{1-22}$ alkyl or $C_{2-22}$ alkenyl radical, and optionally carrying one or more OH groups or represent a group $C_hH_{2h}ZCOR_9$;

$R_6$, $R_7$ and $R_9$, which are identical or different, represent linear or branched $C_{1-22}$ alkyl or $C_{2-22}$ alkenyl radicals optionally carrying one or more OH groups, or $R_7$ may form with part of $R_8$ a heterocycle, n varies from 0 to 500;
q varies from 0 to 20;
a varies from 0 to 50;
b varies from 0 to 50;
c varies from 0 to 4;
 f varies from 0 to 4,
 g varies from 0 to 2,
 h varies from 1 to 4,
Z represents an oxygen atom or NH, and
$A^-$ represents a monovalent inorganic or organic anion, wherein the silicone with quaternary ammonium groups is present in an amount of 0.01 to 10% by weight relative to the total weight of the composition, and at least one fatty alcohol which is liquid at 25° C. and at 1 atm selected from the group consisting of saturated or unsaturated, linear or branched $C_8$-$C_{30}$ fatty alcohols optionally oxyalkylenated with 1 to 15 mol of alkylene oxide or polyglycerolated with 1 to 6 mol of glycerol, wherein the liquid fatty alcohol is present in an amount ranging from 0.01% to 15% by weight relative to the total weight of the composition.

2. The composition as claimed in claim 1, wherein at least one of the following conditions is satisfied:
c is equal to 2 or 3;
$R_1$ denotes the methyl group;
a and b are equal to zero;
n varies from 0 to 100;
q is equal to 0;
f=3;
g=1;
$R_6$ and $R_7$ denote a methyl group;
$R_8$ denotes the radical —$(CH_2)$—$NHCOR_9$.

3. The composition as claimed in claim 1, wherein said silicone is Quaternium-80.

4. The composition as claimed in claim 1, wherein the silicone with quaternary ammonium groups is provided in the form of a solution, suspension or dispersion in water.

5. The composition as claimed in claim 1, wherein the liquid fatty alcohol is selected from the group consisting of lauryl, isostearyl, isocetyl and oleyl alcohols, lauryl alcohols oxyethylenated with 2 to 6 mol of ethylene oxide and mixtures thereof.

6. The composition as claimed in claim 1, wherein the liquid fatty alcohol is present in an amount ranging from 0.1% to 5% by weight relative to the total weight of the composition.

7. The composition as claimed in claim 1, further comprising at least one cationic surfactant.

8. The composition as claimed in claim 7, wherein the cationic surfactant is selected from the group consisting of the salts of optionally polyoxyalkylenated primary, secondary or tertiary fatty amines, quaternary ammonium salts and mixtures thereof.

9. The composition as claimed in claim 8, comprising a quaternary ammonium salt selected from the group consisting of:

those which have the following general formula (V):

in which the symbols $R_1$ to $R_4$, which may be identical or different, represent a linear or branched aliphatic radical containing from 1 to 30 carbon atoms, or an aromatic radical such as aryl or alkylaryl; $X^-$ is an anion selected from the group consisting of halides, phosphates, acetates, lactates, ($C_2$-$C_6$) alkyl sulfates, and alkyl or alkylaryl sulfonates;

the quaternary ammonium salts of imidazoline;

the diquaternary ammonium salts of formula (VII):

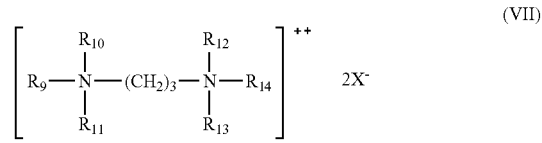

in which $R_9$ denotes an aliphatic radical comprising about from 16 to 30 carbon atoms, $R_{10}$, $R_{11}$, $R_{12}$, $R_{13}$ and $R_{14}$, which are identical or different, are selected from the group consisting of hydrogen or an alkyl radical comprising from 1 to 4 carbon atoms, and $X^-$ is an anion selected from the group consisting of halides, acetates, phosphates, nitrates and methyl sulfates; and the quaternary ammonium salts containing at least one ester functional group.

10. The composition as claimed in claim 8, comprising a quaternary ammonium salt of imidazoline selected from the group consisting of those of the following formula (VI):

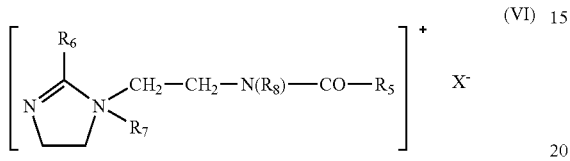

(VI)

in which $R_5$ represents an alkenyl or alkyl radical comprising from 8 to 30 carbon atoms, $R_6$ represents a hydrogen atom, a $C_1$-$C_4$ alkyl radical or an alkenyl or alkyl radical comprising from 8 to 30 carbon atoms, $R_7$ represents a $C_1$-$C_4$ alkyl radical, $R_8$ represents a hydrogen atom, a $C_1$-$C_4$ alkyl radical, X is an anion selected from the group consisting of the group comprising halides, phosphates, acetates, lactates, alkyl sulfates, and alkyl or alkylaryl sulfonates.

11. The composition as claimed claim 7, wherein the cationic surfactant is selected from the group consisting of behenyltrimethylammonium chloride, cetyltrimethylammonium chloride, Quaternium-83, behenylamidopropyl-2,3-dihydroxypropyldimethylammonium chloride and palmitylamidopropyltrimethylammonium chloride.

12. The composition as claimed claim 7, wherein the cationic surfactant is present in an amount of 0.05 to 10% by weight relative to the total weight of the composition.

13. The composition as claimed in claim 1, further comprising at least one cationic polymer.

14. The composition as claimed in claim 13, which comprises at least two different cationic polymers.

15. The composition as claimed in claim 13, wherein the cationic polymer is selected from the group consisting of those cationic polymers which contain units containing primary, secondary, tertiary and/or quaternary amine groups which may either form part of the main polymer chain, or may be carried by a side substituent which is directly attached to it.

16. The composition as claimed in claim 13, wherein said cationic polymer is selected from the group consisting of:

(1) the homopolymers or copolymers derived from acrylic or methacrylic esters or amides and comprising at least one of the units of the following formulae:

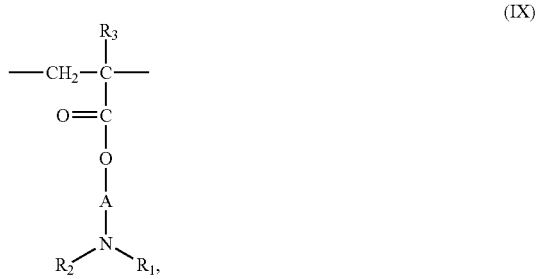

(IX)

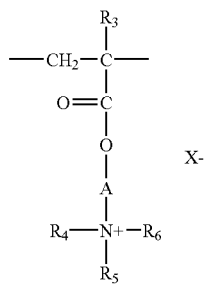

(X)

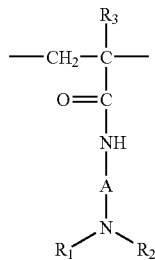

(XI)

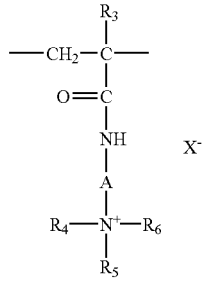

(XII)

in which:
R$_3$, which are identical or different, denote a hydrogen atom or a CH$_3$ radical;
A, which are identical or different, represent a linear or branched alkyl group of 1 to 6 carbon atoms or a hydroxyalkyl group of 1 to 4 carbon atoms;
R$_4$, R$_5$, R$_6$, which are identical or different, represent an alkyl group having from 1 to 18 carbon atoms or a benzyl radical;
R$_1$ and R$_2$, which are identical or different, represent hydrogen or an alkyl group having from 1 to 6 carbon atoms;
X denotes an anion derived from an inorganic or organic acid, (2) cationic polysaccharides,
(3) polymers consisting of piperazinyl units and of alkylene or hydroxyalkylene divalent radicals with straight or branched chains, optionally interrupted by oxygen, sulfur or nitrogen atoms or by aromatic or heterocyclic rings, as well as the oxidation and/or quaternization products of these polymers,
(4) water-soluble polyaminoamides prepared by polycondensation of an acid compound with a polyamine; these polyaminoamides may be crosslinked with an epihalohydrin, a diepoxide, a dianhydride, an unsaturated dianhydride, a diunsaturated derivative, a bishalohydrin, a bisazetidinium, a bishaloacyldiamine, an alkyl bishalide or else with an oligomer resulting from the reaction of a difunctional compound which is reactive toward a bishalohydrin, a bisazetidinium, a bishaloacyldiamine, an alkyl bishalide, an epihalohydrin, a diepoxide or a diunsaturated derivative; the crosslinking agent being employed in proportions ranging from 0.025 to 0.35 mol per amine group of the polyaminoamide; these polyaminoamides may be alkylated or, if they include one or more tertiary amine functional groups, quaternized, (5) polyaminoamides resulting from the condensation of polyalkylenepolyamines with polycarboxylic acids, followed by an alkylation with bifunctional agents, (6) polymers obtained by reaction of a polyalkylenepolyamine containing two primary amine groups and at least one secondary amine group with a dicarboxylic acid selected from the group consisting of diglycolic acid and saturated aliphatic dicarboxylic acids containing from 3 to 8 carbon atoms, (7) cyclopolymers of alkyldiallylamine or of dialkyldiallylammonium, (8) quaternary diammonium polymers containing repeat units corresponding to the formula:

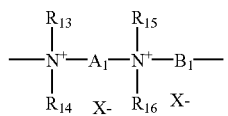

(XIV)

formula (XIV) in which:

$R_{13}$, $R_{14}$, $R_{15}$ and $R_{16}$, which are identical or different, represent aliphatic, alicyclic or arylaliphatic radicals containing from 1 to 20 carbon atoms or lower hydroxyalkylaliphatic radicals, or else $R_{13}$, $R_{14}$, $R_{15}$ and $R_{16}$, together or separately, form, with the nitrogen atoms to which they are attached, heterocycles optionally containing a second heteroatom other than nitrogen, or else $R_{13}$, $R_{14}$, $R_{15}$ and $R_{16}$ represent a linear or branched $C_1$-$C_6$ alkyl radical substituted by a nitrile, ester, acyl, amide or —CO—O—$R_{17}$-D or —CO—NH—$R_{17}$-D group where $R_{17}$ is an alkylene and D a quaternary ammonium group;

$A_1$ and $B_1$ represent polymethylene groups containing from 2 to 20 carbon atoms which may be linear or branched, saturated or unsaturated and which may contain, bonded to or inserted into the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{13}$ and $R_{15}$, with the two nitrogen atoms to which they are attached, may form a piperazine ring; in addition if $A_1$ denotes a saturated or unsaturated, linear or branched alkylene or hydroxyalkylene radical, $B_1$ may also denote a group $(CH_2)_n$—CO-D-OC—$(CH_2)_n$-in which D denotes:

a) a glycol residue of formula: —O—Z—O—, where Z denotes a linear or branched hydrocarbon radical or a group corresponding to one of the following formulae:

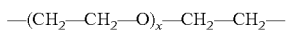

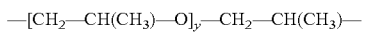

where x and y denote an integer from 1 to 4, representing a defined and unique degree of polymerization or any number from 1 to 4 representing a mean degree of polymerization;

b) a disecondary diamine residue such as a piperazine derivative;

c) a diprimary diamine residue of formula: —NH—Y—NH—, where Y denotes a linear or branched hydrocarbon radical or else the divalent radical

—$CH_2$—$CH_2$—S—S—$CH_2$—$CH_2$—;

d) a ureylene group of formula: —NH—CO—NH—;

(9) polyquaternary ammonium polymers consisting of units of formula (XVI):

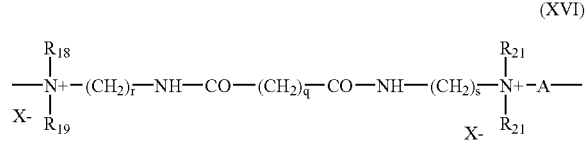

(XVI)

in which formula:

$R_{18}$, $R_{19}$, $R_{20}$ and $R_{21}$, which are identical or different, represent a hydrogen atom or a methyl, ethyl, propyl, β-hydroxyethyl, β-hydroxypropyl or —$CH_2CH_2$$(OCH_2CH_2)_p$ OH radical, where p is equal to 0 or to an integer between 1 and 6, provided that $R_{18}$, $R_{19}$, $R_{20}$ and $R_{21}$ do not simultaneously denote a hydrogen atom, r and s, which are identical or different, are integers between 1 and 6, q is equal to 0 or to an integer between 1 and 34, X denotes a halogen atom, A denotes a radical of a dihalide or preferably represents —$CH_2$—$CH_2$—O—$CH_2$—$CH_2$—,

(10) quaternary vinylpyrrolidone and vinylimidazole polymers,

(11) polyamines,

(12) the crosslinked polymers of methacryloyloxy($C_1$-$C_4$ alkyl)tri($C_1$-$C_4$ alkyl)ammonium salts, and

(13) polyalkyleneimines, polymers containing vinylpyridine or vinylpyridinium units, condensates of polyamines and epichlorohydrin, polyquaternary ureylenes and chitin derivatives.

17. The composition as claimed in claim 16, wherein said cationic polymer is selected from the group consisting of cationic cyclopolymers, cationic polysaccharides, quaternary polymers of vinylpyrrolidone and of vinylimidazole, and mixtures thereof.

18. The composition as claimed in claim 17, wherein said cationic polymer is a cyclopolymer selected from the group consisting of homopolymers of diallyldimethylammonium chloride and copolymers of acrylamide and diallyldimethylammonium chloride.

19. The composition as claimed in claim 17, wherein said cationic polymer is a polysaccharide selected from the group consisting of starches modified with a 2,3-epoxypropyltrimethylammonium salt, guar gums modified with a 2,3-epoxypropyl-trimethylammonium salt and hydroxyethylcelluloses which have reacted with an epoxide substituted with a trimethylammonium group.

20. The composition as claimed in claim 17 wherein said cationic polymer is a quaternary polymer of vinylpyrrolidone and of vinylimidazole selected from the group consisting of copolymers of vinylpyrrolidone and of salts of methylvinylimidazolium.

21. The composition as claimed in claim 14 which comprises at least one cationic polysaccharide and at least one quaternary polymer of vinylpyrrolidone and of vinylimidazole.

22. The composition as claimed in claim 14 which comprises at least one homopolymer of diallyldimethylammonium chloride and at least one quaternary polymer of vinylpyrrolidone and of vinylimidazole.

23. The composition as claimed in claim 13 wherein the cationic polymer is present in an amount ranging from 0.001% to 20% by weight relative to the total weight of the composition.

24. The composition as claimed in claim 1, further comprising at least one thickening agent.

25. The composition as claimed in claim 24, wherein said thickening agent is nonionic.

26. The composition as claimed in claim 25, wherein said nonionic thickening agent is selected from the group consisting of:
   nonionic homopolymers and copolymers containing ethylenically unsaturated monomers of the ester and/or amide type;
   homo- and copolymers of vinylpyrrolidone, and polysaccharides.

27. The composition as claimed in claim 24, wherein said thickening agent is selected from the group consisting of polyacrylamides, methyl methacrylate/ethylene glycol dimethacrylate copolymers, butyl methacrylate/methyl methacrylate copolymers, and polymethyl methacrylates.

28. The composition as claimed in claim 24, wherein said thickening agent is a crosslinked homopolymer of vinylpyrrolidone.

29. The composition as claimed in claim 24, wherein said thickening agent is selected from the group consisting of glucans, modified or unmodified starches, amylose, amylopectin, glycogen, dextrans, celluloses and derivatives thereof (methylcelluloses, hydroxyalkylcelluloses, ethylhydroxyethylcelluloses), mannans, xylans, lignins, arabans, galactans, galacturonans, chitin, chitosans, glucoronoxylans, arabinoxylans, xyloglucans, glucomannans, pectic acids and pectins, arabinogalactans, carrageenans, agars, gums arabic, gums Tragacanth, Ghatti gums, Karaya gums, carob gums, galactomannans and mixtures thereof.

30. The composition as claimed in claim 24, wherein the thickening agent is present in an amount of between 0.001% and 20% by weight relative to the total weight of the composition.

31. The composition as claimed in claim 1, further comprising at least one surfactant selected from the group consisting of anionic, nonionic and amphoteric surfactants.

32. The composition as claimed claim 1, further comprising at least one additional conditioner.

33. The composition as claimed in claim 32, wherein the additional conditioner is selected from the group consisting of silicones, carboxylic esters comprising at least 12 carbon atoms, vegetable oils, mineral oils, synthetic oils and mixtures thereof.

34. The composition as claimed in claim 1, wherein the cosmetically acceptable medium comprises water and, optionally, a cosmetically acceptable solvent.

35. The composition as claimed in claim 34, wherein the medium comprises a cosmetically acceptable solvent selected from the group consisting of $C_1$-$C_4$ lower alcohols, alkylene glycols, polyol ethers, $C_5$-$C_{10}$ alkanes, acetone, methyl ethyl ketone, $C_1$-$C_4$ alkyl acetates, dimethoxyethane, diethoxyethane, and mixtures thereof.

36. The composition as claimed in claim 1 further comprising at least one of the following:
   a anionic, nonionic or amphoteric polymer, a nonpolymeric thickener, an opacifier, a pearlescent agent, a vitamin, a provitamin, a wax, a natural or synthetic ceramide, a perfume, a colorant, organic or inorganic particles, a preservative, or a pH stabilizing agent.

37. The composition as claimed in claim 1, provided in the form of a shampoo, an after-shampoo, a composition for permanent waving, straightening, dyeing or bleaching the hair, a rinse-out composition to be applied between the two stages of a permanent waving or a hair straightening, or a washing composition for the body.

38. The composition as claimed in claim 1, provided in the form of a rinse-out after-shampoo.

39. A method for washing or for treating keratinous materials, comprising applying the composition of claim 1 thereto.

40. A method for making hair shiny, comprising applying the composition of claim 1 to hair in need thereof.

41. A method for making hair supple, comprising applying the composition of claim 1 to hair in need thereof.

42. The composition as claimed in claim 1, wherein the liquid fatty alcohol is selected from the group consisting of: linear and saturated $C_8$-$C_{14}$ fatty alcohols; saturated or unsaturated, branched $C_{12}$-$C_{30}$ fatty alcohols; linear and unsaturated $C_{14}$-$C_{30}$ fatty alcohols; and mixtures thereof, wherein the liquid fatty alcohol is optionally oxyalkylenated with 1 to 15 mol of $C_2$-$C_4$ alkylene oxide.

43. The composition as claimed in claim 1, wherein the liquid fatty alcohol is selected from the group consisting of: linear and saturated $C_8$-$C_{14}$ fatty alcohols; saturated or unsaturated, branched $C_{12}$-$C_{30}$ fatty alcohols; linear and unsaturated $C_{14}$-$C_{30}$ fatty alcohols; and mixtures thereof, wherein the liquid fatty alcohol is optionally oxyalkylenated with 1 to 5 mol of $C_2$-$C_4$ alkylene oxide.

* * * * *